United States Patent [19]

Ochi et al.

[11] 4,179,452
[45] Dec. 18, 1979

[54] 3α,6α-DIHYDROXY-5β-CHOLESTAN-24-ONE DERIVATIVES AND PROCESS FOR PREPARING THE SAME

[75] Inventors: Kiyoshige Ochi, Kawagoe; Isao Matsunaga; Minoru Shindo, both of Tokyo; Chikara Kaneko, Kanazawa, all of Japan

[73] Assignee: Chugai Seiyaku Kabushiki Kaisha, Tokyo, Japan

[21] Appl. No.: 906,866

[22] Filed: May 17, 1978

[30] Foreign Application Priority Data

May 23, 1977 [JP] Japan .................. 52/58815

[51] Int. Cl.² .............................. C07J 9/00
[52] U.S. Cl. .................. 260/397.2; 260/239.55 R
[58] Field of Search ................... 260/397.2; /Steroids MS File

[56] References Cited

U.S. PATENT DOCUMENTS 3,846,455  11/1974  Ikekawa ................ 260/397.2
4,098,801   7/1978  Micheli ................. 260/397.2

FOREIGN PATENT DOCUMENTS 51-100056  9/1976  Japan .

OTHER PUBLICATIONS

Tetrahedron Letters (1972), No. 40, pp. 4147–4150.

Primary Examiner—Elbert L. Roberts
Attorney, Agent, or Firm—Browdy and Neimark

[57] ABSTRACT

3α,6α-Dihydroxy-5β-cholestan-24-one or its derivative represented by the formula

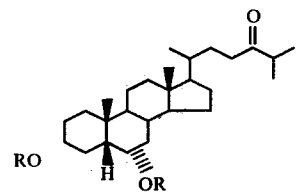

wherein R is as defined hereunder which is a useful intermediate for the production of an active vitamin D, and a process for preparing the compound of the formula are disclosed.

5 Claims, No Drawings

3α,6α-DIHYDROXY-5β-CHOLESTAN-24-ONE DERIVATIVES AND PROCESS FOR PREPARING THE SAME

BACKGROUND OF THE INVENTION

This invention relates to 3α,6α-dihydroxy-5β-cholestan-24-one or its derivatives represented by the formula

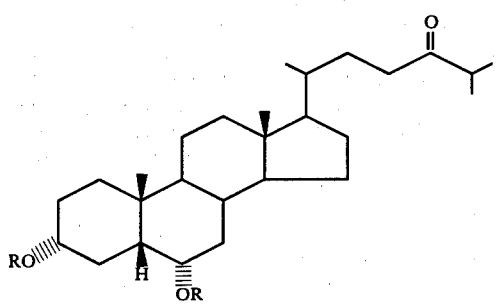

wherein R is hydrogen or a protective group for hydroxyl radical and to a process for preparing the same.

In recent years, extensive research has been carried on for developing compounds which are active metabolites of vitamine D. Especially, steroid compounds having hydroxyl group(s) attached to their side chain, particularly, cholesterol compounds having hydroxyl group(s) at 24 and/or 25 positions, have attracted researchers' attention as an intermediate for the production of active vitamin $D_3$, for example, 1α,25-dihydroxycholecalciferol, 1α,24-dihydroxycholecalciferol, 1α,24,25-trihydroxycholecalciferol, 25-hydroxycholecalciferol, 24,25-dihydroxycholecalciferol or the like.

Desmosterol is known as a useful intermediate for preparing these active vitamin $D_3$ above. In fact, various types of active vitamin $D_3$ are derived from desmosterol. Although desmosterol is very useful as an intermediate for preparing the active vitamin $D_3$, it is difficult to commercially supply it as raw material because, for example, it is derived from fucosterol extracted from certain seaweeds, which is a hardly available natural substance.

The inventors of this invention carefully searched for ways to produce desmosterol or its derivatives and, after intensive research, found that hyodeoxycholic acid, which is easily available, can be used to prepare the compound represented by the formula (I) with several reaction steps. Further, they succeeded in easily preparing desmosterol using the compound (I) above to complete this invention.

According to this invention, the object compound (I) is prepared by reacting a compound represented by the formula

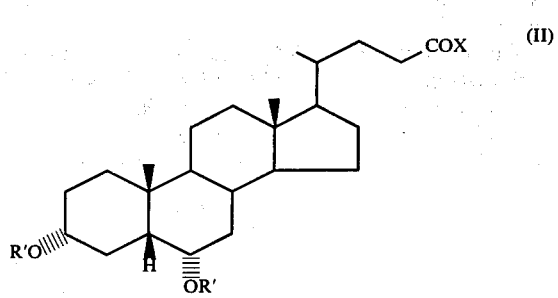

wherein R' is a protecting group for hydroxyl radical and X is halogen, alkoxyl or aralkyloxyl, with an organometallic compound. The organometallic compounds which are useful in this invention include, for example, diisopropyl cadmium, diisopropyl zinc, isopropyl zinc halide and isopropyl magnesium halide.

The compound (II) may be easily prepared by introducing a protective group into hydroxyl groups of hyodeoxycholic acid by the conventional way and then reacting the acid with thionyl chloride, phosphorus oxychloride, phosphorus trichloride or phosphorus pentachloride under heating in the presence of or in the absence of a solvent, for example, benzene, chloroform, etc.

In the practice of the process of this invention, the compound (II) may be reacted with an organometallic compound in the presence of an inert solvent such as benzene, toluene or diethyl ether at a temperature ranging from 0° to 50° C., preferably, from 10° to 30° C. for 1-3 hours to give the object compound (I), the hydroxyl groups of which are protected. If necessary, the compound (I) with the protecting groups may be hydrolized in a conventional manner to remove the protecting group.

Incidentally, if the compound (I) with protecting groups is desired, said group may be conveniently selected from acyl, triarylmethyl, methoxymethyl, tetrahydropyranyl, alkysilyl or benzyl.

Some examples of process for preparation of desmosterol from the compounds of this invention are shown hereunder.

(a) 3α,6α-Dihydroxy-5β-cholestan-24-one (I) is reduced for example by the action of an alkali metal hydride to form 3α,6α,24-trihydroxy-5β-cholestane (III). The reduction may be carried out by adding to a reaction system an alkali metal borohydride, such as potassium borohydride or sodium borohydride, or lithium alminium hydride. The reaction is effected in a solvent such as an ether or an alcohol. Then, the compound (III) is reacted with a chlorinating agent such as phosphorus trichloride, phosphorus pentachloride or phosphorus oxychloride to form 3-chlorocholest-5,24-diene (IV). In this reaction, the hydroxyl groups of compound (III) are chlorinated and then the resulting 3,6,24-trichloro compound is easily dehydrochlorinated simultaneously to give the compound (IV). In the last reaction, any solvent inert to the reaction system can be used. However, an aromatic solvent such as benzene or toluene, or halogenated hydrocarbon such as chloroform, carbon tetrachloride or methylene chloride is usually used, and more preferably, a basic solvent or a base-containing solvent which is an acceptor for hydrogen chloride generated during the reaction is used. The reaction temperature may vary within the range from room temperature to the reflux temperature of the solvent used.

Then, the compound (IV) is converted to 3β-acyloxycholest-5,24-diene (V). This substitution can be effected in a conventional manner, for example, by using potassium acetate in glacial acetic acid. It is confirmed that the compound (V) is the same compound as the acylated desmosterol.

(b) 3α,6α-Dihydroxy-5β-cholestan-24-one (I) is mesylated in a conventional manner to form 3α,6α-dihydroxy-5β-cholestan-24-one dimesylate (VI). Then the compound (VI) is reacted with an inorganic salt such as potassium chloride, sodium chloride or lithium chloride to give 3-chlorocholest-5-en-24-one (VII).

Although the reaction may be carried out in the absence of a solvent, the presence of a solvent is preferred to mildly accelerate the reaction. The kind of solvent suitable for this reaction is one that can easily dissolve an inorganic salt and may be selected from an amide such as dimethylformamide, hexamethylphosphoric triamide or hexamethylphosphoramide, an acetone or an alcohol. The reaction may be carried out at a temperature of from room temperature to an elevated temperature.

The compound (VII) which is prepared above is treated as in (a) above to introduce an acyloxyl group into 3β-position thereby forming 3β-acyloxycholest-5-en-24-one (VIII). The desmosterol derivative (V) as disclosed in (a) above may be easily derived from the compound (VIII) in a conventional manner, for example, as disclosed in Japanese Patent Disclosures Nos. 149662/1975 and 24264/1975.

(c) 3α,6α-Dihydroxy-5β-cholestan-24-one diacetate (I) may be subjected to reduction reaction as in (a) above to give 3α,6α,24-trihydroxy-5β-cholestane 3α,6α-diacetate (IX). The reduction reaction may be conveniently carried out without causing removal of an acyl group, if calcium borohydride is used. The compound (IX) is dehydrated with the aid of an acid catalyst to form 3α,6α-dihydroxy-5β-cholest-24-ene diacetate (X). The presence of a tertiary amine such as pyridine or triethyl amine during the dehydration is preferred in order to increase the reaction rate and to improve the yield. Although any acid catalyst which may be used for such type of dehydration as that above may be utilized, the preferable acid catalysts include, for example, phosphorus oxychloride, thionyl chloride, methansulfonic acid, p-toluenesulfonic acid or its chloride, phosphoric anhydride and sulfuric acid. The compound (X) is hydrolized to form 3α,6α-dihydroxy-5β-cholest-24-ene (XI). The compound (XI) is mesylated in a conventional manner to give 3α,6α-dihydroxy-5β-cholest-24-ene dimesylate (XII). The compound (XII) is treated as in (b) above with the use of an inorganic salt to give 3-chlorocholest-5,24-diene (IV) which is treated as in (a) above to give 3β-acyloxycholest-5,24-diene (V).

This invention is further illustrated by the following Examples.

EXAMPLE 1

The solution of hyodeoxycholic acid (30 g) in acetic anhydride (90 ml) and glacial acetic acid (180 ml) was refluxed for one hour. After cooling, the reaction mixture was evaporated and the residue was dissolved in pyridine (200 ml) and water (40 ml). The mixture was refluxed for one hour and then evaporated. The residue was dissolved in chloroform, and the chloroform layer was washed with water and a diluted aqueous hydrochloric acid, and dried over magnesium sulfate. Chloroform was evaporated to give 31 g of hyodeoxycholic acid diacetate.

IR spectrum (cm$^{-1}$, KBr): 1735, 1708.

NMR spectrum (δ in CDCl$_3$): 0.65 (3H,S), 0.98 (6H,S), 2.01 (3H,S), 2.03 (3H,S), 4.4–5.4 (1H,m).

EXAMPLE 2

To the suspension of metallic magnesium flakes (4.46 g) in dry diethyl ether (200 ml) was added dropwise a solution of isopropyl bromide (18.9 ml) in dry diethyl ether (100 ml) while stirring at room temperature. The mixture was refluxed for 30 minutes to completely dissolve the magnesium flakes. After cooling, anhydrous cadmium bromide (25 g) was slowly added to the solution of isopropyl magnesium bromide and the mixture was refluxed for one hour. Then, diethyl ether was evaporated, and dry benzene was added to the residue to give a solution of diisopropyl cadmium in benzene.

Separately, acetylhyodeoxycholic acid (10 g) was dissolved in thionyl chloride (50 ml) and mildly heated for 30 minutes. After removal of excess thionyl chloride by evaporation under reduced pressure, the resulting diacetylhyodeoxycholic acid chloride was dissolved in dry benzene. To the solution was added dropwise the separately prepared solution of diisopropyl cadmium in benzene while vigorously stirring and then cooling with water. One hour after completion of the addition, water was added to the reaction mixture under cooling with ice-water and then a 5% aqueous solution of hydrochloric acid was added to decompose the excess reagent. The benzene layer was washed with water, dried over magnesium sulfate and evaporated to give an oily product, 3α,6α-dihydroxy-5β-cholestan-24-one diacetate which had a melting point of 108°–109° C. after recrystallization from methanol.

IR spectrum (cm$^{-1}$, KBr): 1730, 1712.

NMR spectrum (δ in CDCl$_3$): 0.66 (3H,S), 0.99 (6H,S), 1.10 (3H,S), 1.94 (6H,S), 4.3–4.8 (1H,m).

EXAMPLE 3

3α,6α-Dihydroxy-5β-cholestan-24-one diacetate prepared in Example 2 was dissolved in a solution of potassium hydroxide (11 g) in methanol (200 ml), and the solution was stirred at room temperature for 3 hours. The reaction mixture was concentrated into about 50 ml in volume. Water was added to the concentrate and the separated oil was extracted with ethyl acetate. The ethyl acetate layer was washed with water, dried over magnesium sulfate and evaporated. The residue was chromatographed on silica gel to give 3 g of 3α,6α-dihydroxy-5β-cholestan-24-one having a melting point of 180°–181° C. after recrystallization from ethyl acetate.

IR spectrum (cm$^{-1}$, KBr): 3360, 1710.

NMR spectrum (δ in CDCl$_3$): 0.64 (3H,S), 0.90 (6H,S), 1.02 (3H,S), 1.14 (3H,S), 3.30–3.80 (2H,m), 3.80–4.40 (2H,m).

EXAMPLE 4

To the solution of 3α,6α-dihydroxy-5β-cholestan-24-one (2.6 g) in methanol (200 ml) was added sodium borohydride (2 g) and stirred for one hour under cooling with ice. After decomposition of excess sodium borohydride with aqueous solution of acetic acid, the mixture was evaporated to reduce the volume to about 100 ml and the residue was extracted with ethyl acetate.

The ethyl acetate layer was washed with water, dried over magnesium sulfate and evaporated to give 2.0 g of 3α,6α,24-trihydroxy-5β-cholestane having a melting point of 169°-173° C. after recrystallization from chloroform.

NMR spectrum (δ in CDCl₃): 0.65 (3H,S), 0.91 (3H,S), 0.97 (3H,S), 3.0-4.3 (3H,m).

EXAMPLE 5

(a) To the solution of 3α,6α,24-trihydroxy-5β-cholestan (1.5 g) in pyridine (20 ml) was added phosphorus oxychloride (3 ml). After completion of the reaction, the reaction mixture was poured into ice-water and extracted with diethyl ether. The ether layer was washed with an aqueous solution of hydrochloric acid and then with water, dried over magnesium sulfate and evaporated to dryness. The residue was chromatographed on silica gel to give 0.6 g of 3-chlorocholest-5,24-diene.

NMR spectrum (δ in CCl₄): 0.69 (3H,S), 0.97 (3H,S), 1.03 (3H,S), 1.58 (3H,S), 1.66 (3H,S), 3.5-3.9 (1H,m) 5.35 (1H,b.S)

(b) To the suspension of the oily product prepared in the process (a) above in glacial acetic acid (20 ml) was added anhydrous potassium acetate (6 g) and then the mixture was refluxed for 2.5 hours. After addition of water, the mixture was extracted with diethyl ether and the resulting ether layer was washed with water, dried and evaporated. The residue was chromatographed on silica gel to give 332.9 mg of desmosterol acetate having a melting point of 92°-93° C. after recrystallization from acetone-methanol. The product was identified with the authentic sample by mixed melting point determination.

EXAMPLE 6

(a) To the solution of 3α,6α-dihydroxy-5β-cholestan-24-one (168 mg) in pyridine (5 ml) was added methanesulfonyl chloride (0.5 ml) under cooling in an ice bath and the mixture was continuously stirred for one hour. The reaction mixture was poured into ice-water and extracted with ethyl acetate. The ethyl acetate layer was washed with an aqueous solution of hydrochloric acid and then with water, dried over magnesium sulfate and evaporated to give an oily product, 3α,6α-dihydroxy-5β-cholestan-24-one dimesylate.

IR spectrum (cm⁻¹, KBr): 1710, 1172, 923.

NMR spectrum (δ in CCl₄): 0.66 (3H,S), 0.99 (6H,S), 1.10 (3H,S), 2.97 (6H,S), 4.3-5.1 (2H,m)

(b) To the solution of 3α,6α-dihydroxy-5β-cholestan-24-one dimesylate prepared (a) above in dimethylformamide (10 ml) was added lithium chloride (100 mg) and the mixture was refluxed for 30 minutes. After cooling, water was added to the reaction mixture and the mixture was extracted with diethyl ether. The ether layer was washed with water, dried over magnesium sulfate and evaporated to give an oily product, 3-chlorocholest-5-en-24-one.

NMR spectrum (δ in CCl₄): 0.68 (3H,S), 0.92 (3H,S), 0.99 (3H,S), 1.02 (3H), 1.00 (3H,S), 5.33 (1H,m).

(c) To the solution of 3-chlorocholest-5-en-24-one in glacial acetic acid (3 ml) was added anhydrous potassium acetate (0.2 g) and the solution was refluxed for 4 hours. The reaction mixture was concentrated and extracted with diethyl ether. The ether layer was washed with water, dried over magnesium sulfate and evaporated. The residue was chromatographed on silica gel to give 81.1 mg of 3β-hydroxycholest-5-en-24-one acetate having a melting point of 125°-127° C. after recrystallization from methanol.

IR spectrum (cm⁻¹, KBr): 1708, 1726.

NMR spectrum (δ in CDCl₃): 0.69 (3H,S), 0.96 (3H,S), 1.03 (6H,S), 1.14 (3H,S), 2.03 (3H,S), 5.60 (1H,m) 5.40 (1H,m).

EXAMPLE 7

(a) 3α,6α-Dihydroxy-5β-cholestan-24-one diacetate was treated with calcium borohydride to give 3α,6α,24-trihydroxy-5β-cholestane diacetate.

IR spectrum (cm⁻¹, KBr): 3380.

NMR spectrum (δ in CCl₄): 0.67 (3H,S), 0.82 (3H,S), 0.93 (3H,S), 1.00 (3H,S), 1.96 (6H,S), 3.20 (1H,m) 4.4-5.25 (2H,m)

The thus prepared 3α,6α,24-trihydroxy-5β-cholestane 3α,6α-diacetate was treated with phosphorus oxychloride in pyridine in the same manner as that of Example 5-(a) and the product was hydrolized in a conventional manner to give 3α,6α-dihydroxy-5β-cholest-24-ene having a melting point of 188°-190° C. after recrystallization from methanol.

IR spectrum (cm⁻¹, KBr): 3380.

NMR spectrum (δ in CCl₄): 0.64 (3H,S), 0.90 (6H,b.S), 1.10 (3H,S), 1.18 (3H,S), 3.30-4.30 (4H,m), 5.1 (1H,m).

(b) To the solution of 3α,6α-dihydroxy-5β-cholestan-24-ene (196.7 mg) in pyridine (10 ml) was added methanesulfonyl chloride (1 ml) and the mixture was stirred under cooling in an ice bath for 2 hours. The reaction mixture was poured into ice-water and extracted with diethyl ether. The ether layer was washed with an aqueous solution of hydrochloric acid and then with water, dried over magnesium sulfate and evaporated to give 190 mg of an oily product, 3α,6α-dihydroxy-5β-cholest-24-ene dimesylate.

To the solution of the product in dimethylformamide (5 ml) was added lithium chloride (0.2 g), and then the solution was refluxed for 20 minutes. The reaction mixture was extracted with diethyl ether and the ether layer was washed with water, dried and evaporated to give 150 mg of 3-chlorocholest-5,24-diene. The product was treated as in Example 5-(b) to give 105.4 mg of desmosterol acetate.

What is claimed is:

1. A 3α,6α-dihydroxy-5β-cholestan-24-one derivative represented by the formula

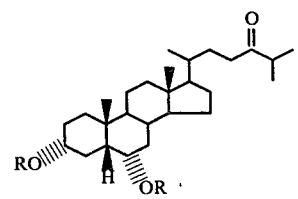

wherein R is hydrogen, acyl, triarylmethyl, methoxymethyl, tetrahydropyranyl, alkylsilyl or benzyl.

2. A 3α,6α-dihydroxy-5β-cholestan-24-one derivative represented by the formula

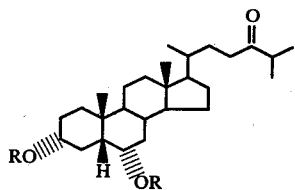
wherein R is hydrogen or acyl.
3. 3α,6α-Dihydroxy-5β-cholestan-24-one according to claim 1.
4. 3α,6α-Dihydroxy-5β-cholestan-24-one diacetate according to claim 1.
5. 3α,6α-Dihydroxy-5β-cholestan-24-one dimesylate according to claim 1.
* * * * *